(12) United States Patent
Lucia et al.

(10) Patent No.: US 12,239,373 B2
(45) Date of Patent: Mar. 4, 2025

(54) DEVICE AND METHOD FOR VISION REHABILITATION

(71) Applicant: Politecnico di Torino, Turin (IT)

(72) Inventors: Umberto Lucia, Alessandria (IT); Giulia Grisolia, Savona (IT); Marco Actis Grande, Cuneo (IT); Bartolomeo Montrucchio, Turin (IT); Maria Rosa Astori, Alessandria (IT); Emilio Paolucci, Turin (IT); Antonio Ponzetto, Moncalieri (IT)

(73) Assignee: Politecnico Di Torino, Turin (IT)

( * ) Notice: Subject to any disclaimer, the term of this patent is extended or adjusted under 35 U.S.C. 154(b) by 467 days.

(21) Appl. No.: 17/629,049

(22) PCT Filed: Jul. 8, 2020

(86) PCT No.: PCT/IB2020/056410
§ 371 (c)(1),
(2) Date: Jan. 21, 2022

(87) PCT Pub. No.: WO2021/014253
PCT Pub. Date: Jan. 28, 2021

(65) Prior Publication Data
US 2022/0265139 A1 Aug. 25, 2022

(30) Foreign Application Priority Data
Jul. 23, 2019 (IT) .................. 102019000012687

(51) Int. Cl.
*A61B 3/024* (2006.01)
*A61H 5/00* (2006.01)
(Continued)

(52) U.S. Cl.
CPC .............. *A61B 3/024* (2013.01); *A61H 5/00* (2013.01); *G16H 20/30* (2018.01); *G16H 40/67* (2018.01)

(58) Field of Classification Search
CPC .......... A61B 3/024; A61H 5/00; A61H 5/005; G16H 20/30; G16H 40/67; A61F 9/00
(Continued)

(56) References Cited

U.S. PATENT DOCUMENTS

| 6,898,454 B2* | 5/2005 | Atalar | H01Q 1/40 600/410 |
| 2004/0176821 A1* | 9/2004 | Delbeke | A61N 1/36046 607/54 |

(Continued)

FOREIGN PATENT DOCUMENTS

WO 2005/000153 A2 1/2005

OTHER PUBLICATIONS

International Search Report and Written Opinion dated Oct. 28, 2020, issued in PCT Application No. PCT/IB2020/056410, filed Jul. 8, 2020.

*Primary Examiner* — Mohammed A Hasan
(74) *Attorney, Agent, or Firm* — Workman Nydegger

(57) ABSTRACT

An apparatus and a method for vision rehabilitation are provided, wherein the apparatus includes a communication component, a visualization component and a processing component configured to receive, through the communication component, a plurality of data that define a visual field of at least one eye of a patient, generate a therapeutic image on the basis of the plurality of data, and visualized, through the visualization component, the therapeutic image, wherein the therapeutic image has geometric and/or chromatic fea-
(Continued)

tures which, if perceived by the patient, stimulate a regeneration of tissues comprised in the visual apparatus of the patient.

10 Claims, 4 Drawing Sheets

(51) Int. Cl.
*G16H 20/30* (2018.01)
*G16H 40/67* (2018.01)

(58) Field of Classification Search
USPC .......................................... 351/224
See application file for complete search history.

(56) References Cited

U.S. PATENT DOCUMENTS

| 2006/0106436 | A1* | 5/2006 | Medes | A61M 21/00 |
| | | | | 607/88 |
| 2006/0161218 | A1* | 7/2006 | Danilov | A61B 5/682 |
| | | | | 607/45 |
| 2006/0164597 | A1* | 7/2006 | Hayakawa | A61H 5/00 |
| | | | | 351/203 |
| 2007/0200927 | A1* | 8/2007 | Krenik | A61B 3/0033 |
| | | | | 348/47 |

* cited by examiner

DEVICE AND METHOD FOR VISION REHABILITATION

BACKGROUND OF THE INVENTION

1. The Field of the Invention

The present invention relates to a device and a method for vision rehabilitation and re-education of partially sighted patients; in particular, the invention is based on the re-education of the patient's retinal nerve fibres through the stimulation of brain plasticity.

2. The Relevant Technology

As is known, low vision is a pathological condition which consists in the reduction of visual acuity and/or visual field. Said condition severely limits the autonomy of the individual, thus compromising the performance of normal daily activities, and therefore constitutes a priority problem for the Health Services of all Countries.

The causes of low vision are manifold and can be the result of eye diseases (including glaucoma, maculopathy, amblyopia) or traumatic events (e.g. accidents, strokes, tumours, surgical operations, etc.).

It is known that, by suitably stimulating the ocular structures, it is possible to induce the regeneration of damaged structures and the consequent vision rehabilitation of partially sighted patients.

Currently, therapeutic eye stimulation techniques are mainly based on the use of waves; in particular, acoustic waves, shock waves and light waves.

These techniques require the use of complex machines for the therapy, which require precise calibration operations and imply that rehabilitation sessions must take place in specialized facilities and in the presence of technical support staff to avoid risks for the patient.

The need to go to specialized facilities to be able to follow the rehabilitation sessions makes it difficult, due to the difficulties in moving of the partially sighted patients and to the need to schedule these sessions, to guarantee a sufficient frequency of sessions to produce an improvement in the patient's visual apparatus in less time.

SUMMARY OF THE INVENTION

In light of this examination, it is therefore a technical problem underlying the invention that of making available a device and a method for vision rehabilitation of partially sighted patients, with characteristics such as to overcome the limits of the state of the art outlined above.

Within the scope of said technical problem, a specific object of the invention is that of making the vision rehabilitation of the patient possible at home without risk for the patient.

A further object of the invention is to allow remote monitoring of patient results.

The idea of solving the aforementioned problem, which also allows to achieve the aforementioned purposes, is to generate therapeutic images based on data that describe the patient's visual field, for example computerized perimetry data, PEV, etc., which can be visualized on the screen of an electronic device available to the patient (for example a smartphone, a tablet, a laptop, etc.).

Further advantageous features of the present invention are object of the attached claims.

BRIEF DESCRIPTION OF THE DRAWINGS

These characteristics and further advantages of the present invention will become clearer from the description of an embodiment thereof shown in the attached drawings, provided purely by way of non-limiting example, in which.

DETAILED DESCRIPTION OF THE PREFERRED EMBODIMENTS

The reference to "an embodiment" within this description indicates that a particular configuration, structure or feature is comprised in at least one embodiment of the invention. Hence, the terms "in one embodiment" and the like, present in different parts within this description, do not necessarily all refer to the same embodiment. Furthermore, the particular configurations, structures or characteristics can be combined in any suitable way in one or more embodiments. The references used below are for convenience only and do not limit the scope of protection or the scope of the embodiments.

Figure 1:
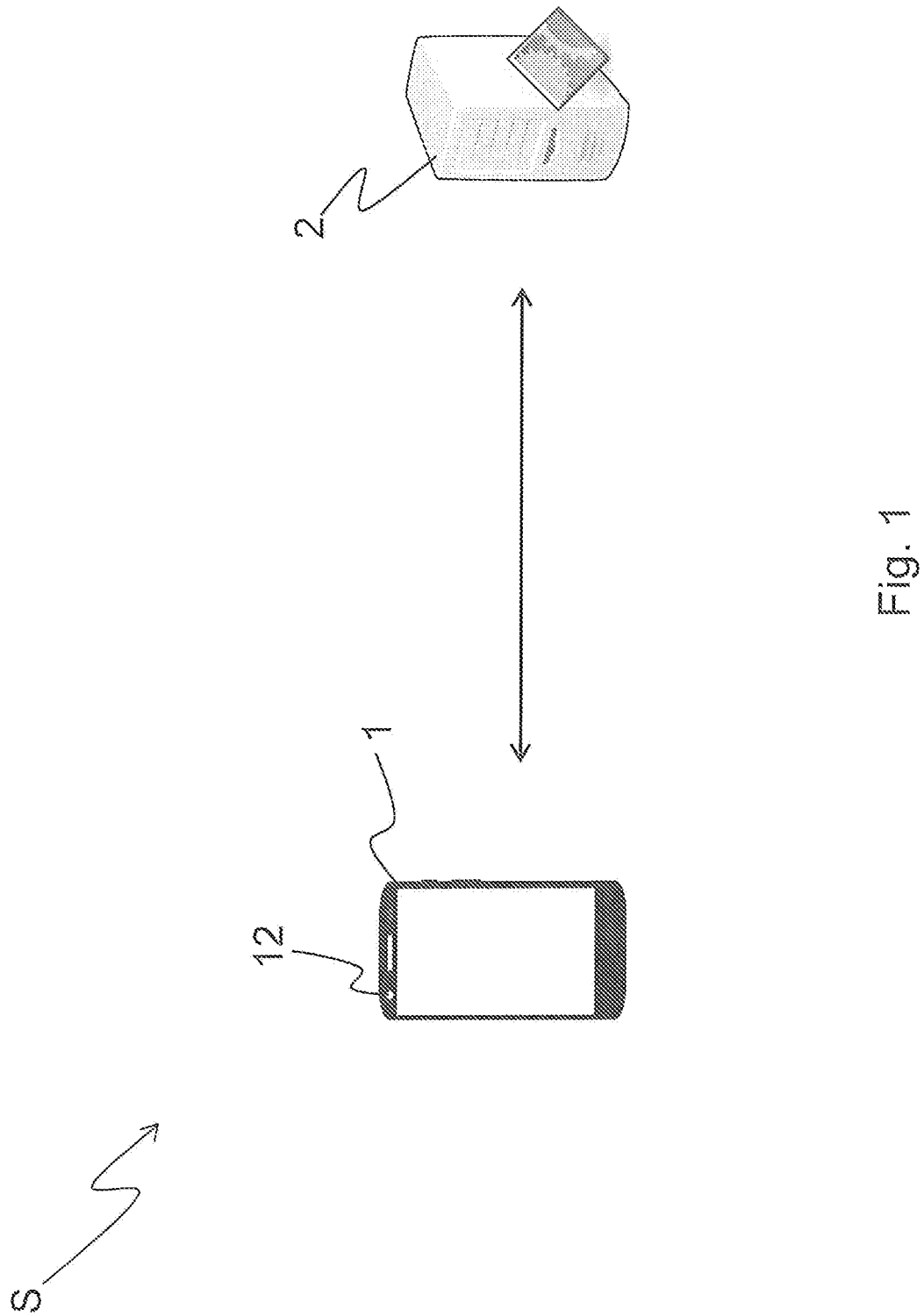
FIG. 1 illustrates a system comprising a device according to the invention.

With reference to FIG. 1, a system S for telemedicine will now be described, comprising a device 1 for vision rehabilitation of partially sighted patients according to the invention; this system S comprises the following parts:

a device 1 for the patient's vision rehabilitation (such as, for example, a smartphone, a tablet, a PC, a laptop or the like) adapted to generate images with variable chromaticity and intensity, defined on the basis of the examination of the patient's visual field and such as to stimulate the ophthalmic structures in order to encourage the re-education of said structures;

an application server 2 which supports the functionality of the device 1; in particular, the application server 2 can be configured to collect and store the patient's data received by the device 1 and manage said data and their transmission (for example the transmission to the ophthalmologist) to allow the remote monitoring of the patient's results. Furthermore, the application server 2 can be provided for processing the received data and configuring the device 1 in accordance with what is determined during processing.

The application server 2 can consist of one or more servers suitably configured to form a cluster.

The device 1 and the application server 2 are in signal communication with each other by means of a data network, preferably a public data network (such as for example the Internet).

Figure 2:
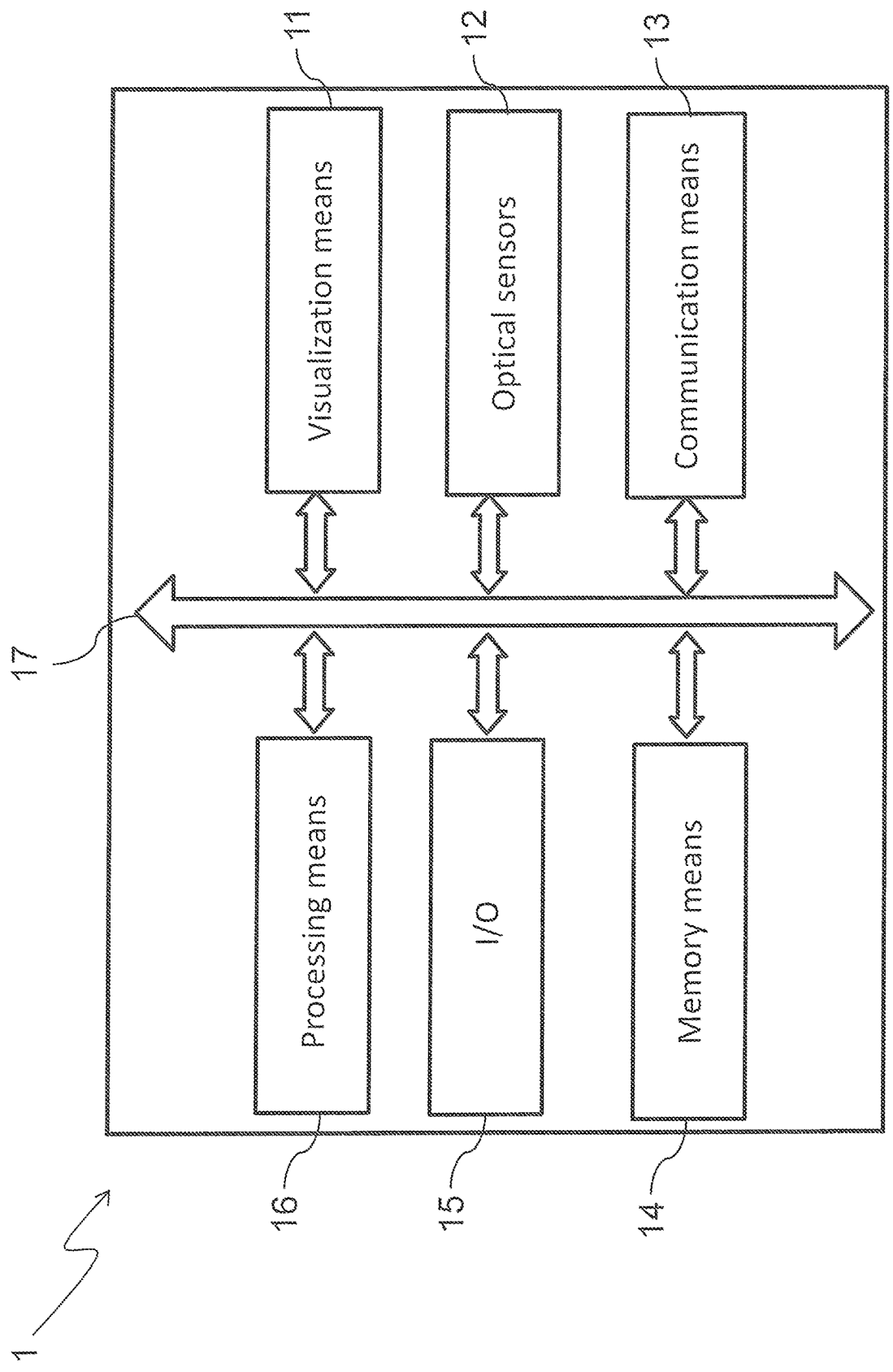
FIG. 2 illustrates a block diagram of the device of FIG. 1.

With reference also to FIG. 2, an embodiment of the device 1 for vision rehabilitation of partially sighted patients preferably comprises the following components:

visualization means 11 (for example the screen of the device 1 or an external screen), which allow to visualize the images generated for the visual re-education of the patient;

optical sensors 12 (such as, for example, photographic or other sensors), preferably comprised (integrated) inside the device 1, to allow the detection of the ocular movements of the patient;

communication means 13, preferably a network interface operating according to a standard of the family 802.11 (known by the name of WiFi), 802.16 (known by the name of WiMax), IEEE 803.2 (also known by the name of Ethernet) or an interface to a GSM/GPRS/UMTS/ LTE, TETRA or other data network, which allow the device 1 to communicate with other devices and, more specifically, to receive and/or transmit data through a telecommunication network, such as for example computerized perimeters or microperimeters which represent the patient's visual field and which are generated by devices for determining the visual field of a patient;

memory means 14, such as for example one or more magnetic disks (hard disk) or a Flash, ROM or other type memory;

input/output (I/O) means 15, which can for example be used to connect peripherals to said device 1 (such as one or more interfaces which allow access to other mass memory means so as to allow preferably the copying of the information therefrom to the memory means 14) or to a programming terminal configured to write instructions (that the processing and control means 11 must execute) in the memory means 14; such input/output means 16 can for example comprise a USB, Firewire, RS232, IEEE 1284 or other adapter;

processing means 16, such as for example one or more CPUs or GPUs, which govern the operation of the device 1 and which are configured to execute a set of instructions which implement the method according to the invention;

a communication bus 17, which allows the exchange of information between the processing means 16, input/output means 15, the memory means 14, the communication means 13, the optical sensors 12 and the visualization means 11.

As an alternative to the communication bus 17, it is possible to connect the processing means 16, the input/output means 15, the memory means 14, the communication means 13, the optical sensors 12 and the visualization means 11 with a star architecture.

Figure 3:
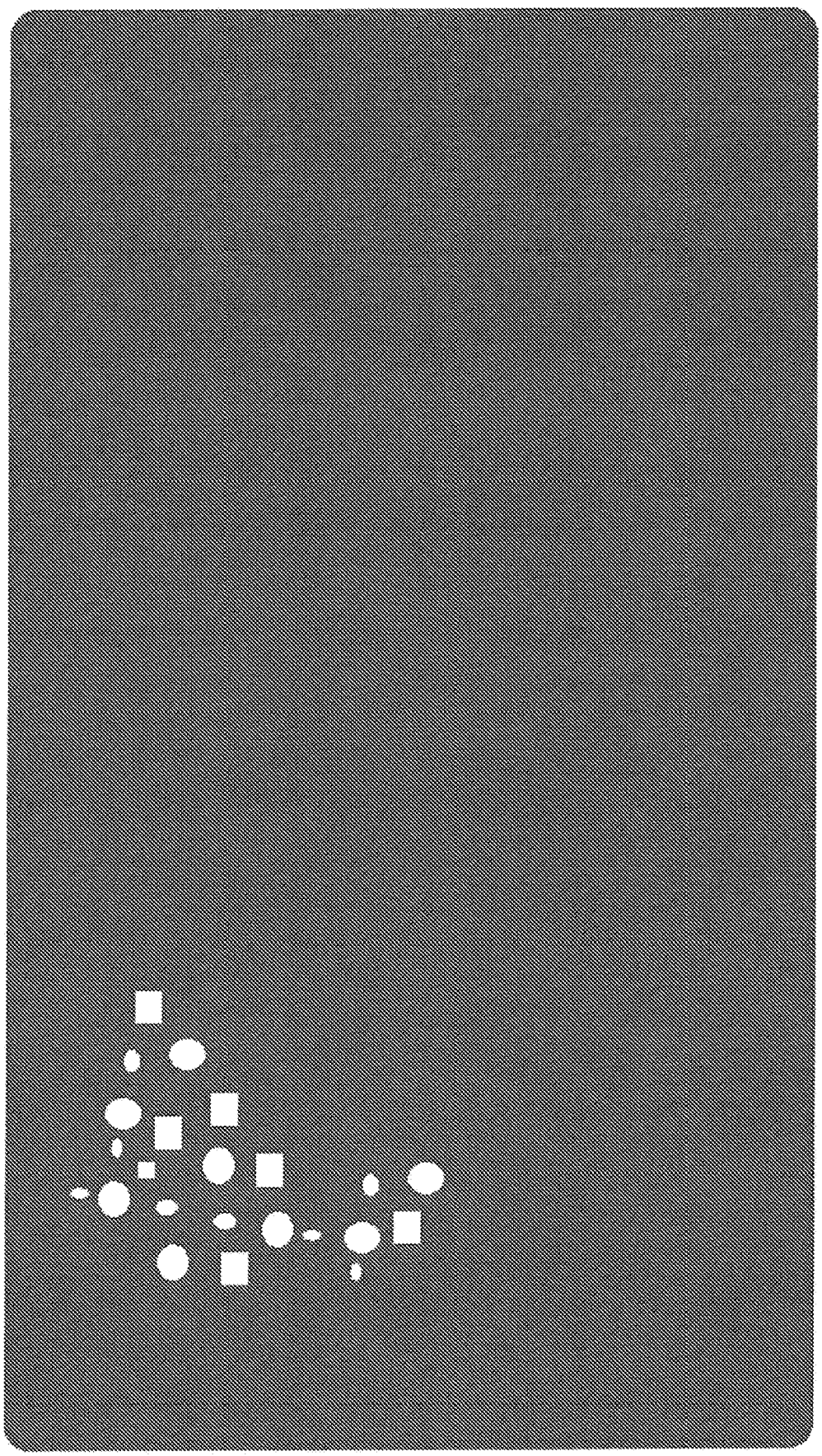
FIG. 3 illustrates a therapeutic image visualized through the device of FIG. 1.

The processing means 16 are configured to receive, through the communication means 13, data that define the visual field of at least one patient's eye, and to generate, based on said data, therapeutic images with variable chromaticity and intensity which can be visualized, through the visualization means 11, and such as to stimulate a regeneration of tissues comprised in the patient's visual apparatus. Preferably, said therapeutic images are geometric and/or point figures (see FIG. 3) which comprise at least one of the following colours, defined according to the frequency and wavelength of the light radiation: 768 nm-432 THz (long magenta), 576 nm-576 THz (yellow), 432 nm-768 THz (cyan), 384 nm-864 THz (short magenta). Furthermore, said images have brightness comprised in the range guaranteed by the electronic devices currently in use to guarantee the non-cytotoxicity of the treatment.

Advantageously, the proposed frequencies and light intensities allow the device 1 to be used in normal working conditions, since the indicated frequencies are normally emitted by the visualization means 11 of said devices 1. Furthermore, the use of these frequencies allows to avoid the risks associated with exposure to light radiation with frequency outside the visible spectrum (such as infrared radiation that can damage the retina).

Preferably, the therapeutic images comprise a viewfinder or pointer (for example a point, a cross or another graphic sign) adapted to draw the patient's attention to a specific point of the therapeutic image and to indicate the position that the eyes must maintain during the entire therapeutic session in order to maximize the effectiveness of the therapy.

Figure 4:
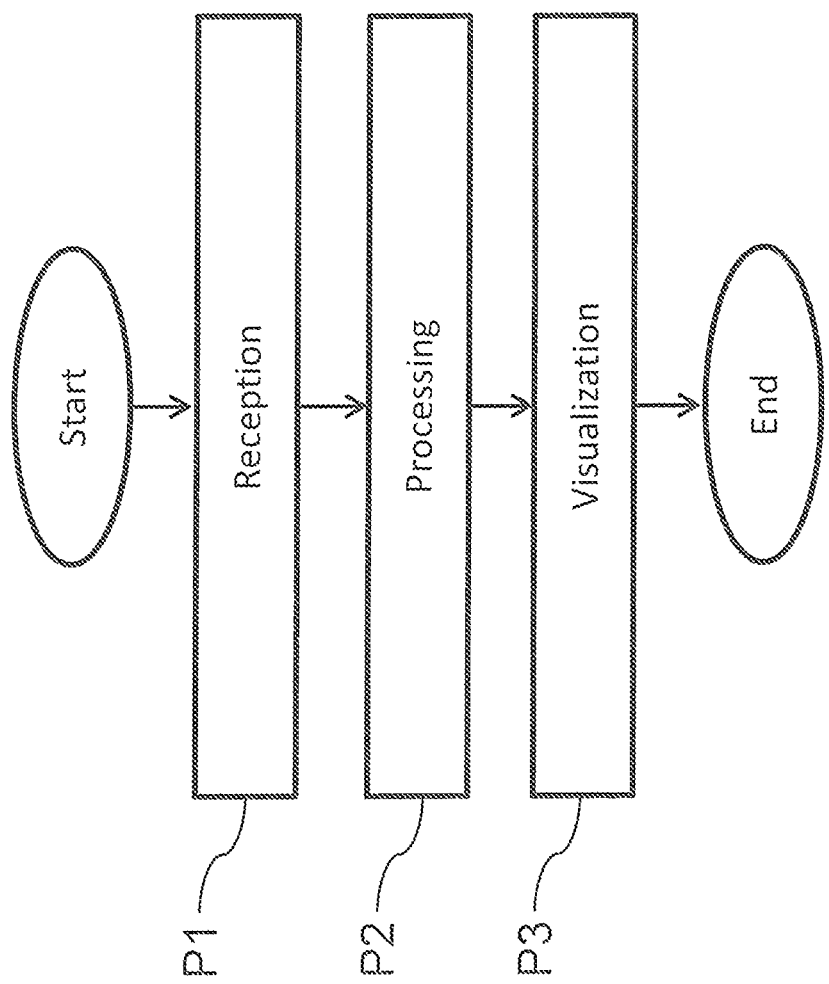
FIG. 4 illustrates a flowchart representing the steps of a method according to the invention.

With reference also to FIG. 4, a method for vision rehabilitation and re-education of partially sighted patients according to the invention will now be described; said method comprises the following steps:

a receiving step P1 in which communication means 13 receive a plurality of data which describe a patient's visual field, for example perimetry data;

a processing step P2, in which, processing means 16 generate a therapeutic image on the basis of the data received in the reception step (P1), therapeutic images with features such as to stimulate a regeneration of the tissues comprised in the patient's visual apparatus, for example by positioning geometric and/or point elements (see FIG. 3) at the limit of the patient's visual field (which is defined by the perimetry data). In other words, said geometric and/or point elements are positioned on the basis of said plurality of data that define the visual field of at least one eye of the patient;

a visualization step P3, in which the generated therapeutic images are visualized through suitable visualization means 11 (such as for example the screen of the device 1).

Some of the possible variants have been described above, but it is clear to the person skilled in the art that, in the practical implementation, other embodiments also exist, with different elements which can be replaced by other technically equivalent ones. The present invention is therefore not limited to the illustrative examples described, but is susceptible of various modifications, improvements, replacements of parts and equivalent elements without involving deviations from the basic inventive idea, as specified in the following claims.

The invention claimed is:

1. A device for vision rehabilitation, comprising:
   communication means for receiving and/or transmitting data through a telecommunication network,
   visualization means for visualizing images, and
   processing means in communication with the communication means and the visualization means,
   wherein the processing means are configured to:
      receive, through the communication means, a plurality of data that define a visual field of at least one eye of a patient,
      generate a therapeutic image on the basis of the plurality of data, and
      visualize, through the visualization means, the therapeutic image, and
   wherein the therapeutic image has geometric and/or chromatic features that, if perceived by the patient, stimulate a regeneration of retinal tissues comprised in a visual apparatus of the patient.

2. The device according to claim 1, wherein the therapeutic images contain geometric elements such as triangles, circles and squares.

3. The device according to claim 1, wherein the therapeutic images comprise at least one element having a colour with frequency comprised in a range of a human visible spectrum.

4. The device according to claim 3, wherein the colour of the at least one element has a frequency equal to 432 THz, 576 THz, 768 THz, or 864 THz.

5. The device according to claim 1, wherein the therapeutic image comprises a viewfinder or pointer adapted to indicate a point in the therapeutic image towards which the patient's eyes must turn.

6. The device according to claim 1, wherein the data that define the patient's visual field are data obtained from a perimetry test.

7. The device according to claim 1, wherein the therapeutic image comprises geometric and/or point elements, and
wherein the processing means are configured to generate the therapeutic image by positioning the geometric and/or point elements on the basis of the plurality of data that define the visual field of at least one eye of the patient.

8. A method for vision rehabilitation, comprising:
a receiving phase in which, through communication means, a plurality of data are received, wherein the data describe a patient's visual field,
a processing phase in which, through processing means, a therapeutic image is generated on the basis of the data received in the receiving phase, wherein the therapeutic image has geometric and/or chromatic features which, if perceived by the patient, stimulate a regeneration of retinal tissues comprised in a visual apparatus of the patient, and
a visualization phase in which, through a visualization means, the therapeutic image is visualized.

9. The method according to claim 8, wherein the therapeutic image comprises geometric and/or point elements, and
wherein, during the processing phase, the therapeutic image is generated by positioning the geometric and/or point elements on the basis of the plurality of data that define the visual field of at least one eye of the patient.

10. A non-transitory computer-readable storage medium including computer-executable instructions that can be loaded into a memory of a computer and executed by a processor of the computer for actuating phases of the method according to claim 8.

* * * * *